United States Patent
Li et al.

(10) Patent No.: US 10,190,154 B2
(45) Date of Patent: Jan. 29, 2019

(54) REDUCED GRAPHENE OXIDE-BASED BIOSENSORS

(71) Applicant: McMaster University, Hamilton (CA)

(72) Inventors: Yingfu Li, Dundas (CA); John D. Brennan, Dundas (CA); Meng Liu, Dundas (CA)

(73) Assignee: McMaster University, Hamilton (CA)

( * ) Notice: Subject to any disclaimer, the term of this patent is extended or adjusted under 35 U.S.C. 154(b) by 0 days.

(21) Appl. No.: 15/091,778

(22) Filed: Apr. 6, 2016

(65) Prior Publication Data

US 2016/0289733 A1    Oct. 6, 2016

Related U.S. Application Data

(60) Provisional application No. 62/143,256, filed on Apr. 6, 2015.

(51) Int. Cl.
*C12Q 1/6806* (2018.01)
*C12Q 1/6844* (2018.01)
*C12Q 1/682* (2018.01)
*C12Q 1/6823* (2018.01)
*G01N 33/53* (2006.01)

(52) U.S. Cl.
CPC .......... *C12Q 1/6806* (2013.01); *C12Q 1/682* (2013.01); *C12Q 1/6823* (2013.01); *C12Q 1/6844* (2013.01); *G01N 33/5308* (2013.01)

(58) Field of Classification Search
CPC .......... C12M 1/00; C12Q 1/6844; C12Q 1/68; G01N 33/5308
See application file for complete search history.

(56) References Cited

U.S. PATENT DOCUMENTS

2011/0294125 A1* 12/2011 Li .......................... C12Q 1/25
435/6.11

OTHER PUBLICATIONS

Liu et al, Biological and chemical sensors based on graphene materials, 2012, Chem. Soc. Rev., 41, 2283-2307. (Year: 2012).*
Data sheet SEQ ID No. 5 search results—PDB, pp. 1-12, printed on Oct. 25, 2017 (Year: 2017).*
Liu, Meng, et al., "A Graphene-Based Biosensing Platform Based on the Release of DNA Probes and Rolling Circle Amplification", ACS Nano, vol. 8, No. 6, May 25, 2014, pp. 5564-5573.

* cited by examiner

*Primary Examiner* — Narayan K Bhat
(74) *Attorney, Agent, or Firm* — Bereskin & Parr LLP/S.E.N.C.R.L., s.r.l.; Patricia Folkins

(57) ABSTRACT

The present application discloses a biosensor that comprises a nucleic acid probe absorbed on reduced graphene oxide, the nucleic acid probe comprising an RCA primer sequence linked to a recognition moiety for an analyte to be detected by the biosensor.

18 Claims, 6 Drawing Sheets

Specification includes a Sequence Listing.

Figure 3

| Name | Sequence | RE | SD |
|---|---|---|---|
| CTA5 | CACAC......AGCCC........AACTACAACA | 43.4 | 2.3 |
| CTA5M1 | ..........AGCCC......CACACAACTACAACA | 36.2 | 1.6 |
| CTA5M2 | CACACAACTAAGCCC..............CAACA | 33.4 | 2.9 |
| CTA5M3 | CACAC......CAACA............AACTAAGCCC | 39.6 | 1.6 |
| CTA5M4 | ........AGCCCCACACA....AACTACAACA | 41.1 | 1.8 |
| CTA5M5 | C.A..ACA.G..AAC.C..CAA.C..TCC.C..AA | 40.5 | 1.0 |

SEQUENCE LISTING

<160> NUMBER OF SEQ ID NOS: 40

<210> SEQ ID NO 1
<211> LENGTH: 35
<212> TYPE: DNA
<213> ORGANISM: Artificial Sequence
<220> FEATURE:
<223> OTHER INFORMATION: Synthetic

<400> SEQUENCE: 1
aacaataccc atcaagcacc aaccacattt cacac         35

<210> SEQ ID NO 2
<211> LENGTH: 35
<212> TYPE: DNA
<213> ORGANISM: Artificial Sequence
<220> FEATURE:
<223> OTHER INFORMATION: Synthetic

<400> SEQUENCE: 2
cacacatact acaactaccc aacacaatat cccac         35

<210> SEQ ID NO 3
<211> LENGTH: 35
<212> TYPE: DNA
<213> ORGANISM: Artificial Sequence
<220> FEATURE:
<223> OTHER INFORMATION: Synthetic

<400> SEQUENCE: 3
acaaacctca cacacataca aacccattat ctcca         35

<210> SEQ ID NO 4
<211> LENGTH: 35
<212> TYPE: DNA
<213> ORGANISM: Artificial Sequence
<220> FEATURE:
<223> OTHER INFORMATION: Synthetic

<400> SEQUENCE: 4
caagaacaac acacacccat aacaattcct ctaac         35

<210> SEQ ID NO 5
<211> LENGTH: 35
<212> TYPE: DNA

```
<213> ORGANISM: Artificial Sequence
<220> FEATURE:
<223> OTHER INFORMATION: Synthetic

<400> SEQUENCE: 5
cacacatcaa agcccatact acaacaacta caaca                              35

<210> SEQ ID NO 6
<211> LENGTH: 35
<212> TYPE: DNA
<213> ORGANISM: Artificial Sequence
<220> FEATURE:
<223> OTHER INFORMATION: Synthetic

<400> SEQUENCE: 6
ctcacataaa acaaacacca cttaaaacac acacc                              35

<210> SEQ ID NO 7
<211> LENGTH: 35
<212> TYPE: DNA
<213> ORGANISM: Artificial Sequence
<220> FEATURE:
<223> OTHER INFORMATION: Synthetic

<400> SEQUENCE: 7
aaaagaacaa caagcacaca catacccca aatac                               35

<210> SEQ ID NO 8
<211> LENGTH: 35
<212> TYPE: DNA
<213> ORGANISM: Artificial Sequence
<220> FEATURE:
<223> OTHER INFORMATION: Synthetic

<400> SEQUENCE: 8
acacccaccg caataataaa aaccacaact tacca                              35

<210> SEQ ID NO 9
<211> LENGTH: 35
<212> TYPE: DNA
<213> ORGANISM: Artificial Sequence
<220> FEATURE:
<223> OTHER INFORMATION: Synthetic

<400> SEQUENCE: 9
ccaaaatagc acaaacacac acacatacct taaac                              35

<210> SEQ ID NO 10
<211> LENGTH: 35
<212> TYPE: DNA
<213> ORGANISM: Artificial Sequence
<220> FEATURE:
<223> OTHER INFORMATION: Synthetic

<400> SEQUENCE: 10
aagaacaaac acttccccat accacacaac atcaa                              35

<210> SEQ ID NO 11
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(50)
<223> OTHER INFORMATION: n is a, c, g, or t
```

<400> SEQUENCE: 11
atctcgacta gtcagnnnnn nnnnnnnnnn nnnnnnnnnn nnnnnnnnnn tgtctcggat          60

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
tagtcgagat atccgagaca          20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
tgtctcggat atctcgacta          20

<210> SEQ ID NO 14
<211> LENGTH: 51
<212> TYPE: DNA
<213> ORGANISM: Artificial Sequence
<220> FEATURE:
<223> OTHER INFORMATION: Synthetic

<400> SEQUENCE: 14
ttcggaagag atggcgacgc cgaactatct ctcgagctga tcctgatgga a          51

<210> SEQ ID NO 15
<211> LENGTH: 60
<212> TYPE: DNA
<213> ORGANISM: Artificial Sequence
<220> FEATURE:
<223> OTHER INFORMATION: Synthetic

<400> SEQUENCE: 15
atctcgacta gtcagaacaa tacccatcaa gcaccaacca catttcacac tgtctcggat          60

<210> SEQ ID NO 16
<211> LENGTH: 60
<212> TYPE: DNA
<213> ORGANISM: Artificial Sequence
<220> FEATURE:
<223> OTHER INFORMATION: Synthetic

<400> SEQUENCE: 16
atctcgacta gtcagcacac atcaaagccc atactacaac aactacaaca tgtctcggat          60

<210> SEQ ID NO 17
<211> LENGTH: 60
<212> TYPE: DNA
<213> ORGANISM: Artificial Sequence
<220> FEATURE:
<223> OTHER INFORMATION: Synthetic

<400> SEQUENCE: 17
atctcgacta gtcagaagaa caaacacttc cccataccac acaacatcaa tgtctcggat          60

<210> SEQ ID NO 18

<211> LENGTH: 60
<212> TYPE: DNA
<213> ORGANISM: Artificial Sequence
<220> FEATURE:
<223> OTHER INFORMATION: Synthetic

<400> SEQUENCE: 18
atctcgacta gtcagcacat acaacacaca aatcaccaac aacacaacat tgtctcggat    60

<210> SEQ ID NO 19
<211> LENGTH: 60
<212> TYPE: DNA
<213> ORGANISM: Artificial Sequence
<220> FEATURE:
<223> OTHER INFORMATION: Synthetic

<400> SEQUENCE: 19
atctcgacta gtcagaataa tcaaacaaca ccacaactat caaaatacca tgtctcggat    60

<210> SEQ ID NO 20
<211> LENGTH: 60
<212> TYPE: DNA
<213> ORGANISM: Artificial Sequence
<220> FEATURE:
<223> OTHER INFORMATION: Synthetic

<400> SEQUENCE: 20
atccgagaca gtgtgaaatg tggttggtgc ttgatgggta ttgttctgac tagtcgagat    60

<210> SEQ ID NO 21
<211> LENGTH: 60
<212> TYPE: DNA
<213> ORGANISM: Artificial Sequence
<220> FEATURE:
<223> OTHER INFORMATION: Synthetic

<400> SEQUENCE: 21
atccgagaca tgttgtagtt gttgtagtat gggctttgat gtgtgctgac tagtcgagat    60

<210> SEQ ID NO 22
<211> LENGTH: 60
<212> TYPE: DNA
<213> ORGANISM: Artificial Sequence
<220> FEATURE:
<223> OTHER INFORMATION: Synthetic

<400> SEQUENCE: 22
atccgagaca ttgatgttgt gtggtatggg gaagtgtttg ttcttctgac tagtcgagat    60

<210> SEQ ID NO 23
<211> LENGTH: 60
<212> TYPE: DNA
<213> ORGANISM: Artificial Sequence
<220> FEATURE:
<223> OTHER INFORMATION: Synthetic

<400> SEQUENCE: 23
atccgagaca atgttgtgtt gttggtgatt tgtgtgttgt atgtgctgac tagtcgagat    60

<210> SEQ ID NO 24
<211> LENGTH: 60
<212> TYPE: DNA
<213> ORGANISM: Artificial Sequence
<220> FEATURE:
<223> OTHER INFORMATION: Synthetic

<400> SEQUENCE: 24

```
atccgagaca tggtattttg atagttgtgg tgttgtttga ttattctgac tagtcgagat    60
```

<210> SEQ ID NO 25
<211> LENGTH: 60
<212> TYPE: DNA
<213> ORGANISM: Artificial Sequence
<220> FEATURE:
<223> OTHER INFORMATION: Synthetic

<400> SEQUENCE: 25

```
atctcgacta gtcagacaac atcaaagccc atactcacac aactacaaca tgtctcggat    60
```

<210> SEQ ID NO 26
<211> LENGTH: 60
<212> TYPE: DNA
<213> ORGANISM: Artificial Sequence
<220> FEATURE:
<223> OTHER INFORMATION: Synthetic

<400> SEQUENCE: 26

```
atctcgacta gtcagcacac aactaagccc atactacaac atcaacaaca tgtctcggat    60
```

<210> SEQ ID NO 27
<211> LENGTH: 60
<212> TYPE: DNA
<213> ORGANISM: Artificial Sequence
<220> FEATURE:
<223> OTHER INFORMATION: Synthetic

<400> SEQUENCE: 27

```
atctcgacta gtcagcacac atcaacaaca atactacaac aactaagccc tgtctcggat    60
```

<210> SEQ ID NO 28
<211> LENGTH: 60
<212> TYPE: DNA
<213> ORGANISM: Artificial Sequence
<220> FEATURE:
<223> OTHER INFORMATION: Synthetic

<400> SEQUENCE: 28

```
atctcgacta gtcagatact atcaaagccc cacacacaac aactacaaca tgtctcggat    60
```

<210> SEQ ID NO 29
<211> LENGTH: 60
<212> TYPE: DNA
<213> ORGANISM: Artificial Sequence
<220> FEATURE:
<223> OTHER INFORMATION: Synthetic

<400> SEQUENCE: 29

```
atctcgacta gtcagcaaaa acatgtcaac ccaacaaacc atccactcaa tgtctcggat    60
```

<210> SEQ ID NO 30
<211> LENGTH: 60
<212> TYPE: DNA
<213> ORGANISM: Artificial Sequence
<220> FEATURE:
<223> OTHER INFORMATION: Synthetic

<400> SEQUENCE: 30

```
atctcgacta gtcaggtttc ctttccttga aacttcttcc tttcctttac tgtctcggat    60
```

<210> SEQ ID NO 31
<211> LENGTH: 37
<212> TYPE: DNA

```
<213> ORGANISM: Artificial Sequence
<220> FEATURE:
<223> OTHER INFORMATION: Synthetic

<400> SEQUENCE: 31
ggttggtgtg gttggaatag tcgagatatc cgagaca                                37

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
gcctcaactt atccgagaca                                                   20

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
atctcgacta gtcaggcact                                                   20

<210> SEQ ID NO 34
<211> LENGTH: 78
<212> TYPE: DNA
<213> ORGANISM: Artificial Sequence
<220> FEATURE:
<223> OTHER INFORMATION: Synthetic

<400> SEQUENCE: 34
aatgatacgg cgaccaccga gatctacact ctttccctac acgacgctct tccgatctgc       60
ctcaacttat ccgagaca                                                     78

<210> SEQ ID NO 35
<211> LENGTH: 84
<212> TYPE: DNA
<213> ORGANISM: Artificial Sequence
<220> FEATURE:
<223> OTHER INFORMATION: Synethic

<400> SEQUENCE: 35
caagcagaag acggcatacg agatttcttg gtgactggag ttcagacgtg tgctcttccg       60
atctatctcg actagtcagg cact                                              84

<210> SEQ ID NO 36
<211> LENGTH: 35
<212> TYPE: DNA
<213> ORGANISM: Artificial Sequence
<220> FEATURE:
<223> OTHER INFORMATION: Synthetic

<400> SEQUENCE: 36
acaacatcaa agcccatact cacacaacta caaca                                  35

<210> SEQ ID NO 37
<211> LENGTH: 35
<212> TYPE: DNA
<213> ORGANISM: Artificial Sequence
<220> FEATURE:
<223> OTHER INFORMATION: Synthetic
```

```
<400> SEQUENCE: 37
cacacaacta agcccatact acaacatcaa caaca                               35

<210> SEQ ID NO 38
<211> LENGTH: 35
<212> TYPE: DNA
<213> ORGANISM: Artificial Sequence
<220> FEATURE:
<223> OTHER INFORMATION: Synthetic

<400> SEQUENCE: 38
cacacatcaa caacaatact acaacaacta agccc                               35

<210> SEQ ID NO 39
<211> LENGTH: 35
<212> TYPE: DNA
<213> ORGANISM: Artificial Sequence
<220> FEATURE:
<223> OTHER INFORMATION: Synthetic

<400> SEQUENCE: 39
atactatcaa agccccacac acaacaacta caaca                               35

<210> SEQ ID NO 40
<211> LENGTH: 35
<212> TYPE: DNA
<213> ORGANISM: Artificial Sequence
<220> FEATURE:
<223> OTHER INFORMATION: Synthetic

<400> SEQUENCE: 40
caaaaacatg tcaacccaac aaaccatcca ctcaa                               35
```

REDUCED GRAPHENE OXIDE-BASED BIOSENSORS

RELATED APPLICATIONS

The present application claims the benefit of provisional patent application No. 62/143,256, filed Apr. 6, 2015, the contents of which are herein incorporated by reference.

INCORPORATION OF SEQUENCE LISTING

A computer readable form of the Sequence Listing "3244-P48282US02_SequenceListing.txt" (8,192 bytes), submitted via EFS-WEB and created on Apr. 6, 2016, is herein incorporated by reference.

FIELD

The present application is in the field of biosensors. In particular the present application is in the field of nucleic acid-based biosensors that utilize rolling circular amplification.

BACKGROUND

Rolling circle amplification (RCA) involves growing a long DNA chain with a repetitive sequence by continuously adding nucleotides to a primer annealed to a circular DNA template.[1,2] The DNA polymerases used for this reaction, such as phi29 DNA polymerase, are special because they possess both strand displacement ability and high processivity.[3,4] These properties empower these enzymes to make cyclic copying of the same circular template, producing extremely long DNA molecules with thousands of sequence repeats.

RCA has emerged as a popular DNA amplification technique because it offers some key advantages that cannot be matched by polymerase chain reaction (PCR). One advantage is that it does not require equipment: while PCR needs temperature cycling, RCA is an isothermal process. No need for special equipment makes RCA better suited for point-of-care (POC) and field applications. Another advantage is the compatibility with most molecular recognition elements (MREs). Unlike PCR that requires a high-temperature (>90° C.) step that deactivates most MREs, RCA can be conducted at temperatures that are more suited for optimal MRE functions. This particular benefit facilitates the use of RCA for the detection of not only nucleic acid targets (both DNA and RNA),[5-8] but also other analytes (small molecules, proteins and even cells)[9-11] when combined with functional nucleic acid probes (e.g. aptamers and DNAzymes).[12-16] The key element in nearly all reported biosensing strategies involving RCA is linking a molecular recognition event into the formation of a primer-template complex from which the DNA polymerase synthesizes long-chain DNA amplicons. Such coupling delivers high detection sensitivity, which is crucial for diagnostic and biosensing applications.

SUMMARY

A biosensing experiment was conducted where an RCA circular template, reduced graphene oxide (rGO) and a DNA aptamer were used to achieve protein detection. This method features a rGO-adsorbed DNA probe that contains an aptamer sequence at its 5' end and a primer for RCA at its 3' end. In the presence of the cognate target, the DNA probe is released from the rGO surface, which is captured by the circular template to enable the RCA reaction for signal amplification. The well-known model thrombin-binding DNA aptamer[20] was used for this demonstration.

Accordingly, in one embodiment, the present application includes a biosensor comprising:

a) reduced graphene oxide (rGO); and b) a nucleic acid probe absorbed on the rGO, the nucleic acid probe comprising an RCA primer sequence linked to a recognition moiety.

Any recognition moiety that is able to detect the presence of an analyte is used, for example, an aptamer that changes conformation in the presence of the analyte, a DNAzyme that cleaves RNA in the presence of the analyte, or an antibody or nucleic acid probe that binds the analyte.

In another embodiment, the present application includes a method for detection of an analyte comprising:

a) contacting a sample suspected of comprising the analyte with a biosensor of the application under conditions for binding the analyte to the recognition moiety and desorption of the nucleic acid probe from the rGO, to provide rGO and an analyte-nucleic acid probe complex;

b) separating the rGO from the analyte-nucleic acid probe complex;

c) contacting the analyte-nucleic acid probe with a circular template comprising a sequence that is complementary to the RCA primer sequence under RCA conditions to amplify the circular template; and d) detecting a presence or an absence of the amplified circular template, wherein the presence of the amplified circular template indicates the presence of the analyte in the sample.

In another embodiment, the present application includes a kit for detection of an analyte comprising a biosensor of the application, a circular template comprising a sequence that is complementary to the RCA primer sequence and reagents to perform RCA.

In one embodiment, the analyte is a nucleic acid, protein or small molecule.

In an embodiment, the circular template comprises a region complementary to the RCA primer and an AC rich nucleotide region. In embodiment, the AC rich nucleotide region is at least 70% AC rich, at least 80% AC rich, or at least 85% AC rich.

In a particular embodiment, the AC rich nucleotide region comprises one of the sequences as shown in SEQ ID NOs: 1-10 or a variant thereof. In another embodiment, the AC rich nucleotide region comprises a scrambled sequence that contains the nucleotide content of one of the sequences shown in SEQ ID NOs: 1-10 or a variant thereof, such as the CTA5 mutants shown in SEQ ID NOs:36-40 or variants thereof. In an embodiment, the variant maintains substantially the same amount of adenine and cytosine as the reference sequence.

In an embodiment, the rolling circle amplification conditions comprise the presence of phi29-, Bst- or Vent exo- DNA polymerase. In an embodiment, the rolling circle amplification conditions comprise the presence of phi29- DNA polymerase.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

The embodiments of the application will now be described in greater detail with reference to the attached drawings in which:

FIG. 3 shows the RCA efficiency comparison of CTA5 and CTA5 mutants (SEQ ID NOs:5, 36, 37, 38, 39 and 40, respectively) in an exemplary embodiment of the application. ARU values that were used to derive RE values are provided in Table 2.

DETAILED DESCRIPTION

I. Definitions

Figure 1:
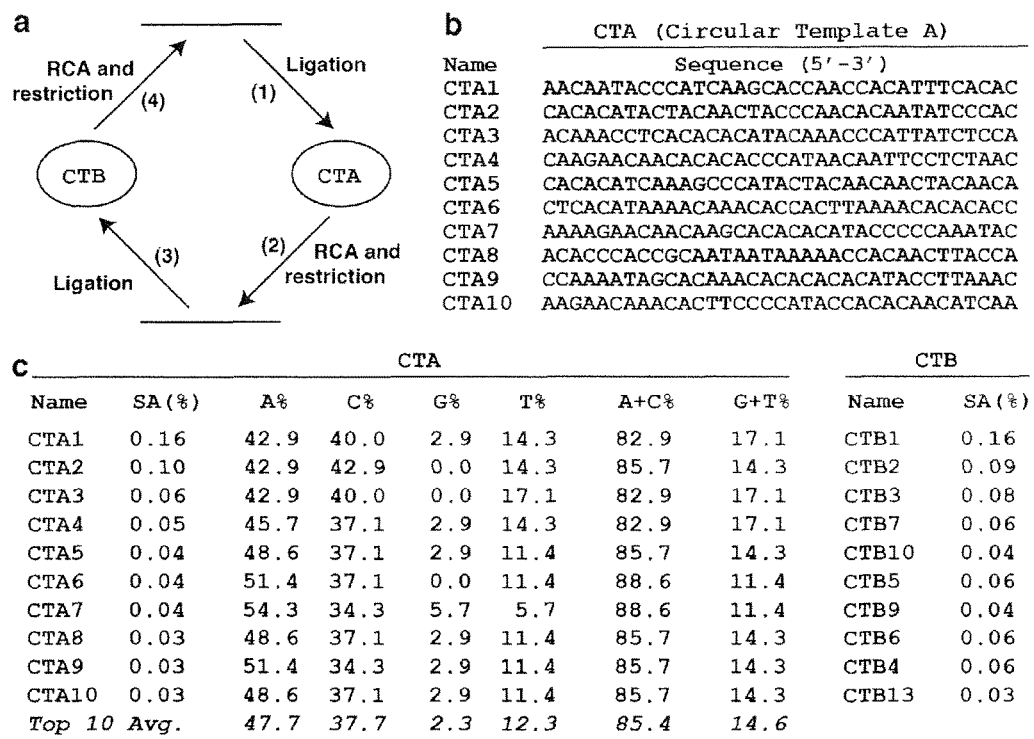
FIG. 1 shows an in vitro selection of optimal DNA templates for RCA in one embodiment of the application. (a) In vitro selection scheme. (b) The top 10 CTA sequences (SEQ ID NOs:1-10 respectively). Only the random-sequence domain is shown. (c) The sequence abundance (SA) and nucleotide distributions of the top 10 CTAs, and their matching CTBs.

Unless otherwise indicated, the definitions and embodiments described in this and other sections are intended to be applicable to all embodiments and aspects of the present application herein described for which they are suitable as would be understood by a person skilled in the art.

The term "analyte" as used herein means any agent, including, but not limited to, nucleic acids, small inorganic and organic molecules, metal ions, hormonal growth factors, biomolecules, toxins, biopolymers (such as carbohydrates, lipids, peptides and proteins), cells, tissues and microorganisms (including bacteria and viruses), for which one would like to sense or detect. In an embodiment, the analyte is either isolated from a natural source or is synthetic. The term analyte also includes mixtures of compounds or agents such as, but not limited to, combinatorial libraries and samples from an organism or a natural environment.

The term "AC rich nucleotide region" as used herein refers to a nucleic acid sequence that has at least 65%, at least 70%, at least 75%, at least 80% or at least 85% content made of adenine (A) and/or cytosine (C) residues. In the Examples section, the AC rich nucleotide region corresponds to the 35 nt random nucleotide region when it is enriched for adenine and cytosine.

The term "nucleic acid" refers to polynucleotides such as deoxyribonucleic acid (DNA) and ribonucleic acid (RNA).

The term "recognition moiety" as used herein refers to an agent that is able to recognize the presence of an analyte. Recognition moieties, include without limitation, aptamers, structure-switching aptamers, reporter aptamers, DNAzymes, antibodies and nucleic acid probes.

The term "aptamer" as used herein refers to short, chemically synthesized, single stranded (ss) RNA or DNA oligonucleotides which fold into specific three-dimensional (3D) structures that bind to a specific analyte with dissociation constants, for example, in the pico- to nano-molar range.

The term "structure-switching nucleic acid aptamers" or "reporter nucleic acid aptamers" as used herein refers to aptamer-based reporters that function by switching structures from a DNA/DNA or RNA/RNA complex to a DNA/analyte or RNA/analyte complex.

The term "concatemeric nucleic acid molecules" or "concatemer" as used herein refers to a long continuous DNA or RNA molecule that contains multiple copies of the same DNA or RNA sequences linked in a tandem series.

The term "rolling circle amplification" as used herein refers to a unidirectional nucleic acid replication that can rapidly synthesize multiple copies of circular molecules of DNA or RNA. In an embodiment, rolling circle amplification is an isothermal enzymatic process where a short DNA or RNA primer is amplified to form a long single stranded DNA or RNA using a circular DNA template and an appropriate DNA or RNA polymerase. The product of this process is a concatemer containing ten to thousands of tandem repeats that are complementary to the circular template.

The phrase "detecting the product of the rolling circle amplification" as used herein refers to detection of concatemers, for example, by colorimetric, electrochemical and/or spectroscopic methods. For example, the recognition moiety may be an aptamer that changes conformation in the presence of an analyte allowing the primer to anneal to the circular template to allow for rolling circle amplification and the concatemer produced is detected using a labelled probe that is complementary to a portion of the product. Other biosensing strategies that utilize rolling circle amplification are known in the art and are encompassed herein.

The term "primer" as used herein refers to a nucleic acid sequence, whether occurring naturally as in a purified restriction digest or produced synthetically, which is capable of acting as a point of synthesis when placed under conditions in which synthesis of a primer extension product, which is complementary to a nucleic acid strand is induced (e.g. in the presence of nucleotides and an inducing agent such as DNA polymerase and at a suitable temperature and pH). The primer is sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less. The factors involved in determining the appropriate length of primer are readily known to one of ordinary skill in the art. A primer can be a DNA, an RNA, or a chimeric DNA/RNA sequence.

The term "probe" refers to a nucleic acid sequence that will hybridize to a nucleic acid target sequence. In one example, the probe hybridizes to the circular template or its complement. The length of probe depends on the hybridization conditions and the sequences of the probe and nucleic acid target sequence. In one embodiment, the probe is 8-100, 8-200 or 8-500 nucleotides in length, such as 8-10, 11-15, 16-20, 21-25, 26-50, 51-75, 76-100, 101-150 or 151-200 nucleotides in length or at least 200, 250, 400, 500 or more nucleotides in length. In other embodiments, 10, 15, 20 or 25 nucleotides provide a lower end for the aforementioned nucleotide ranges.

The term "circular template" as used herein refers to a nucleic acid sequence of at least 20 nucleotides that is ligated to form a circular nucleic acid molecule that can serve as a template for rolling circle amplification.

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. One non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present application. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules. When utilizing BLAST, Gapped BLAST, and PSI-Blast programs, the default parameters of the respective programs (e.g., of XBLAST and NBLAST) can be used (see, e.g., the NCBI website). Another non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.–16.6 (Log 10 [Na+])+0.41(% (G+C)–600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In some embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm–5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

As used in this specification and the appended claims, the singular forms "a", "an" and "the" include plural references unless the content clearly dictates otherwise.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this application and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "and/or" as used herein means that the listed items are present, or used, individually or in combination. In effect, this term means that "at least one of" or "one or more" of the listed items is used or present.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

II. Biosensor and Kits

In one embodiment, the present application includes a biosensor comprising:
reduced graphene oxide (rGO); and
a nucleic acid probe absorbed on the rGO, the nucleic acid probe comprising an RCA primer sequence linked to a recognition moiety for an analyte.

In some embodiments, the recognition moiety is an aptamer that changes conformation in the presence of the analyte, a DNAzyme that cleaves RNA in the presence of the analyte, or an antibody.

In some embodiments, the recognition moiety is an aptamer that changes conformation in the presence of the analyte and binding of the analyte to the aptamer results in desorption of the nucleic acid probe from the rGO. In some embodiments, the recognition moiety is an antibody or a nucleic acid probe specific for the analyte. In some embodiments, the recognition moiety is, without limitation, a structure-switching aptamer or an RNA-cleaving DNAzyme.

In some embodiments, the analyte is a nucleic acid, protein or small molecule.

In some embodiments, the recognition moiety for the analyte is at the 5' end of the probe and the RCA primer sequence is at the 3' end of the probe.

In some embodiments, the nucleic acid probe is labelled with a detectable marker such as a radioactive label which provides a detectable signal and has sufficient half-life, such as $^{32}P$, $^{3}H$, $^{14}C$ or the like. In some embodiments, other detectable markers are used including, for example, antigens that are recognized by a specific labelled antibody, fluorescent compounds, enzymes, antibodies specific for a labelled antigen, and chemiluminescent compounds. In some embodiments, an appropriate label is selected having regard to the rate of hybridization and binding of the probe to the analyte to be detected and the amount of analyte available for binding.

In some embodiments, the primer is labelled with detectable markers for detection of the amplified product. In some embodiments, the detectable markers are radioactive markers, such as $^{32}P$, $^{35}S$, $^{125}I$, and $^{3}H$, luminescent markers, such as chemiluminescent markers (such as luminol), fluorescent markers, such as dansyl chloride, fluorescein-5-isothiocyanate, and 4-fluor-7-nitrobenz-2-axa-1,3 diazole, enzyme markers such as horseradish peroxidase, alkaline phosphatase, β-galactosidase, acetylcholinesterase, or biotin.

In some embodiments, the primer contains non-complementary sequences provided that a sufficient amount of the primer contains a sequence which is complementary to a region of a circular template which is to be amplified, to allow hybridization of the primer to the circular template.

In some embodiments, the primer is linked to a recognition moiety that detects the presence of an analyte. In some embodiments, the recognition moiety is a functional nucleic acid probe, such as an aptamer that changes conformation in the presence of the analyte, or a DNAzyme that cleaves an RNA linkage in the presence of the analyte.

In another embodiment, the present application also includes a kit for detection of an analyte comprising (i) a biosensor of the application; (ii) a circular template comprising a sequence that is complementary to the RCA primer sequence; (iii) one or more RCA reagents; and optionally (iv) instructions for use.

In some embodiments, the one or more RCA reagents are selected from one or more of a DNA polymerase, dNTPs, labelled probes and a reaction buffer. In some embodiments, the DNA polymerase is phi29-, Bst- or Vent exo-DNA polymerase. In some embodiments, the DNA polymerase is phi29 DNA polymerase.

In some embodiments, the circular template circular template comprises a sequence that is complementary to the RCA primer sequence and an AC rich nucleotide sequence.

In some embodiments, the AC rich nucleotide sequence is at least 70% AC rich, at least 80% AC rich, or at least 85% AC rich.

In some embodiments, the AC rich nucleotide sequence comprises one of the sequences as shown in SEQ ID NOs: 1-10 or a variant thereof. In some embodiments, the AC rich nucleotide sequence comprises a scrambled sequence that contains the nucleotide content of one of the sequences shown in SEQ ID NOs: 1-10 or a variant thereof. For example, in some embodiments, the AC rich nucleotide sequence comprises CTA5 (SEQ ID NO:5) scrambled sequences: CTA5M1, CTA5M2, CTA5M3, CTA5M4 and CTA5M5 (SEQ ID NOs:36-40) or variants thereof. A person skilled in the art could readily create similar scrambled sequences of CTA1-4 (SEQ ID NOs:1-4) and CTA6-10 (SEQ ID NOs:6-10) as well as other CTA5 (SEQ ID NO:5) scrambled sequences.

In some embodiments, the variant sequence has at least 50%, or at least 60%, or at least 70%, or at least 80%, or at least 90%, or at least 95% sequence identity to the sequences disclosed herein. In some embodiments, the variant has substantially the same AC content as the reference sequence.

In another embodiment, the variants provided herein include nucleotide sequences that hybridize to the nucleic acid sequences under at least moderately stringent hybridization conditions.

III. Methods

In another embodiment, the present application includes a method for detection of an analyte comprising:

a) contacting a sample suspected of comprising the analyte with a biosensor of the application under conditions for binding the analyte to the recognition moiety and desorption of the nucleic acid probe from the rGO, to provide rGO and an analyte-nucleic acid probe complex;

b) separating the rGO from the analyte-nucleic acid probe complex;

c) contacting the analyte-nucleic acid probe with a circular template comprising a sequence that is complementary to the RCA primer sequence under RCA conditions to amplify the circular template; and d) detecting a presence or an absence of the amplified circular template, wherein the presence of the amplified circular template indicates the presence of the analyte in the sample.

In some embodiments, the circular template comprises a sequence that is complementary to the RCA primer sequence and an AC rich nucleotide sequence as defined above.

In some embodiments, the method further comprises selecting a linear sequence comprising a sequence complementary to the primer and an AC rich nucleotide sequence, followed by circularizing the sequence to form the circular template prior to c). In some embodiments, the circularization is performed using DNA ligase, such as T4 DNA ligase.

In some embodiments, detection by the recognition moiety of the analyte results in desorption of the nucleic acid probe from the rGO permitting the primer to anneal to the circular template whereas in the absence of analyte, the nucleic acid probe remains absorbed to the rGO.

In some embodiments, the analyte is immobilized on a solid support and the recognition moiety then binds to the analyte on the solid support, resulting in desorption of the nucleic acid probe from the rGO and permitting the primer to anneal to the circular template producing a RCA product that is immobilized on the solid support. In such an embodiment, detection of the rolling circle amplification product occurs after the solid support is washed. In some embodiments, the solid support is a nanoparticle, metal surface, inorganic surface, organic surface, paper surface or modified paper surface.

In some embodiments, the analyte is a nucleic acid, protein or small molecule.

Rolling circle amplification conditions are known in the art. For example, rolling circle amplification occurs in the presence of a polymerase that possesses both strand displacement ability and high processivity in the presence of template, primer and nucleotides. In some embodiments, rolling circle amplification conditions comprise temperatures of from about 25° C. to about 35° C., or about 30° C., a reaction time sufficient for the generation of detectable amounts of amplicon and performing the reaction in a buffer. In some embodiments, the rolling circle amplification conditions comprise the presence of phi29-, Bst- or Vent exo- DNA polymerase. In some embodiments, the rolling circle amplification conditions comprise the presence of phi29 DNA polymerase.

In some embodiments, rGO is produced by reducing an aqueous solution of graphene oxide, prepared, for example as described in M. Liu, et al. *ACS Nano* 2012, 6, 3142-3151, with a reducing agent, such as ascorbic acid and ammonia, followed by heating, for example to about 80° C. to about 100° C. for about 3 to about 10 minutes. Cooling this solution to room temperature provides a stably dispersed rGO solution.

The following non-limiting examples are illustrative of the present application:

Examples

Results

The present inventor developed a selection strategy illustrated in FIG. 1a. The method features three enzymatic reactions: templated DNA circularization catalyzed by T4 DNA ligase, RCA by phi29 DNA polymerase, and restriction digestion by EcoRV (FIG. 1a).

The original linear DNA pool (made of $\sim 10^{14}$ 60-nt DNA molecules with a 35-nt random region; nt: nucleotide) was first end-ligated into circular template (denoted CTA; step 1). Following RCA and restriction conversion of long RCA products into monomers (step 2), end-ligation was again performed to produce a new circular template, CTB (step 3). The cycle was completed with another RCA and restriction digestion (step 4). seven iterations of steps 1-4 were performed. To derive the best templates, the amount of CTA and CTB was reduced from 100 pmol in round 1 (R1) to 10 pmol in R2, 1 pmol in R3-R5, and 0.1 pmol in R6 and R7.

The monomeric DNA pool following the step 2 of R7 was subjected to deep sequencing to acquire individual CTA sequences. 296,430 sequence reads were obtained and they can be classified into 235,315 distinct classes. FIG. 1b lists the sequences of the random nucleotide portion of the top 10 CTAs, Consistent with the observed sequence diversity, the top ranked sequence, CTA1, only had a sequence abundance (SA, percentage of a given sequence in the sequenced pool) of 0.16%. Likewise, the accumulative SA of the top 10 sequences was only 0.58%. These observations are not entirely surprising considering DNA polymerases are evolved by nature to copy diverse DNA templates.

The top 10 sequences were found to be highly rich in A and C (85.4%; top 10 average) and poor in G and T (14.6%), especially in G (only 2.3%). This feature also applied to the top 100, 1,000 and 10,000 sequences: these respective groups exhibited an average AC content of 83.2, 81.7 and 80.2% (the corresponding SA values are 1.64, 4.78 and 16.06%). In fact, CTA sequences as a whole showed a significant AC bias (76.1%). As a control experiment, the original DNA pool was also sequenced and only a small bias toward AC (58.1%) was found.

Next, the DNA pool was sequenced following the step 4 of R7 to gather sequence information on CTBs. 580,491 sequence reads were obtained, which can be classified into 433,639 distinct classes. As expected, CTB sequences exhibit an overall bias towards G and T: the average GT content of the top 10, 100, 1,000 and 10,000 sequences is 85.7, 84.9, 83.8 and 82.2%, respectively, reflecting the fact that CTBs are the complements of CTAs. The top 3 CTBs match the top 3 CTAs in the correct order (FIG. 1c). However, the CTB counterparts of CTA4-10, though most of which fall within the top 10, have a different ranking order (FIG. 1c).

Taken together, the results discussed above are indicative of a successful sequence enrichment experiment. However, the great sequence diversity called for experimental confirmation that these sequences were enriched due to better RCA efficiencies.

Figure 6:
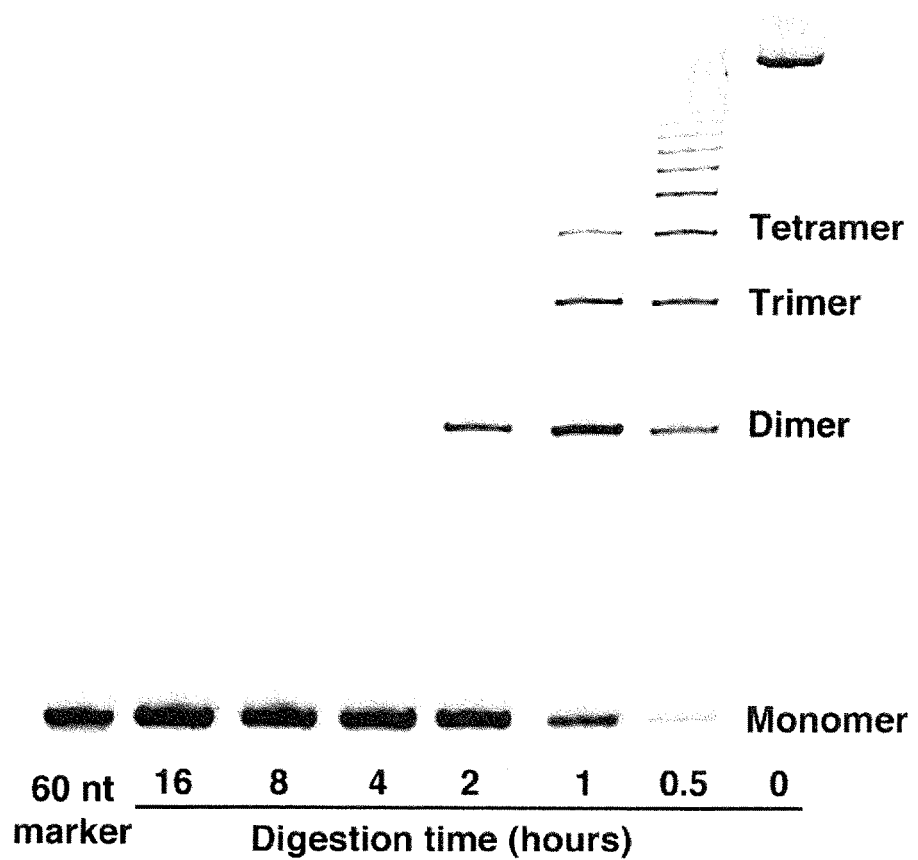
FIG. 6 shows time-dependent digestion of RCA products made from CTA1 using EcoRV in an exemplary embodiment of the application. The RCA reaction was performed at 30° C. for 20 min in 50 µL of 1×RCA buffer containing 0.4 nM CTA1, 2 µM DT1, 1 mM each of dGTP, dATP, dTTP, dCTP, and 5 U phi29 DNA polymerase. The digestion reaction was performed at 37° C. for 0.5, 1, 2, 4, 8 and 16 h in 10 µL made of 5 µL of the above RCA reaction mixture, 2 µL of 50 µM DT2, and 1 µL of 10× Fast Digestion Buffer and 2 µL of FastDigest EcoRV. DT2 was added to make the EcoRV recognition site into double stranded DNA to facilitate the restriction digestion. The reaction mixture was then subjected to dPAGE analysis.

Because it is difficult to directly quantify long-chain RCA products, a strategy was developed that first converts RCA products into monomeric amplicons via digestion with EcoRV, followed by denaturing polyacrylamide gel electrophoresis (dPAGE) and DNA staining with SYBR Gold, a fluorescent DNA binding dye. FIG. 6 shows the result of digesting the RCA product made with CTA1. A full digestion was achieved after 4 hours; a 16-hour digestion was chosen for the remainder of the study to ensure complete monomerization. Because the fully digested RCA product is 60-nt long, a 51-nt DNA molecule with a defined concentration was included as an internal control. By determining the fluorescence ratio (FR) of the two DNA bands in each lane, the concentration of the digested monomer (CM) could be calculated, which was used to estimate the average repeat unit (ARU) of the RCA product based on the input concentration of the circular template.

The method was applied to compare the RCA efficiency (RE) of CTA1 and CTB1, with the inclusion of the original random-sequence DNA library (LB) as the control. FIG. 2a lists FR and ARU values determined for time-dependent RCA of the three templates and FIG. 2b plots ARU values vs. RCA time. The RE of each template was measured as the slope of line.

The above analysis revealed that CTA1 performed ~7-fold better than the control (39.0 vs. 6.1 in RE). It also showed that, although there were two RCA reactions in each selection cycle (steps 1 and 3, FIG. 1a), the template for the first RCA was the driver of the selection (the RE of CTB1 is less than 2-fold higher than that of LB). This observation was consistent with the fact that the first RCA reaction was directly linked to the initial DNA pool.

The RCA efficiency of a few more CTA/CTB pairs was also analyzed and their RE values are provided in FIG. 2c. CTA5 and CTA10 were selected as additional top 10 sequences because their AC content and ACGT distribution (both measured in percentage) closely match the top 10 average values (see FIG. 1c). CTA109 was included because it has an AC content (91.4%) higher than the top 10 average (85.4%). Finally, CTA1548 was chosen because, although lowly ranked, it has top 10-like AC content (85.7%). For comparison, all CTB counterparts of the chosen CTAs were included for the RE analysis.

Like CTA1, both CTA5 and CTA10 were highly efficient RCA templates (RE=43.4 and 36.5, respectively). In comparison, both CTA109 and CTA1548 were less effective as templates (RE=25.9 and 26.4, respectively). As expected, all CTBs had smaller RE values (RE between 7-12). The RE results presented above indicate: (1) the top 10 CTAs were enriched because they can function as better RCA templates; (2) CTAs have an competitive edge over CTBs.

The data in FIG. 2c also suggests other factors beyond high AC content may contribute to the RE of a DNA template. These may include the requirement of a defined sequence and an optimal ACGT composition. To probe into these possibilities, mutagenesis studies of CTA5, the best performing template, were carried out. Five CTA5 mutants were prepared that have the same ACGT composition of CTA5 but vary in sequence arrangements (FIG. 3). The first four mutants differed from their parent in two relocated 5-nt elements and the final mutant was highly scrambled. All five mutants performed similarly as the RCA templates and this observation indicated that the high RCA efficiency of CTA5 was sequence-independent. All considered, the top ranked CTAs have been selected for both its high AC content and optimal ACGT composition, but not for their precise sequences.

Figure 4:
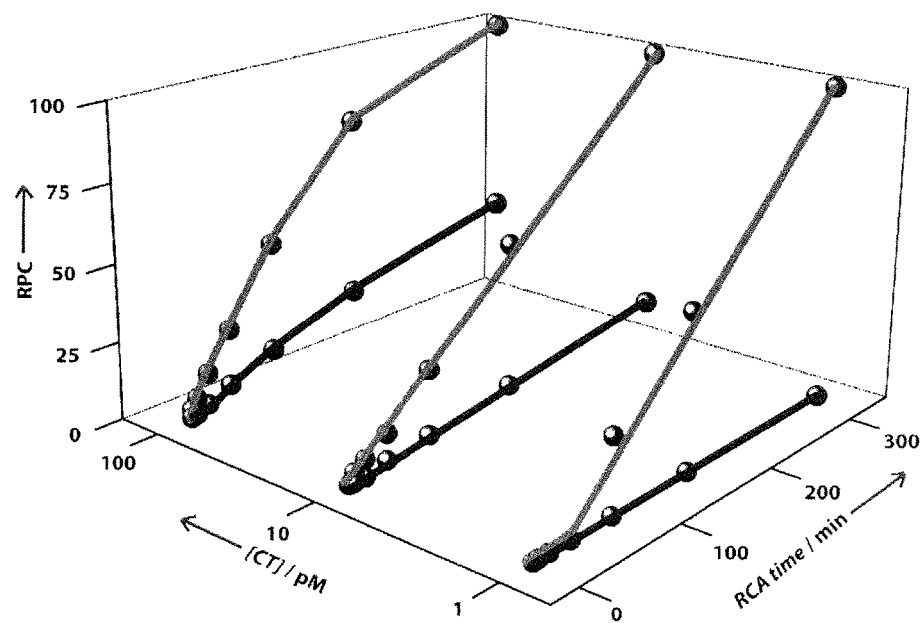
FIG. 4 is a comparison of time-dependent amplicon production using CTA5 (grey line) and LB (black line) as the circular templates in an exemplary embodiment of the application. RPC: relative production of RCA product at a given template concentration. CT: circular template. RPC=100×$C_{M, t}/C_{M, 320}$ where CM, t is the concentration of digested RCA product of CTA5 or LB at time t and CM, 320 is the concentration produced from CTA5 at 320 min.

To further demonstrate the competitive advantage of high-performing templates at low primer-template concentrations, comparative RCA reactions with CTA5 and LB were carried out at varying template concentrations (1, 10 and 100 pM) and RCA times (5-320 min). The concentration of monomeric amplicon (CM) following RCA-digestion-dPAGE steps was then calculated and provided in Table 2. To simplify the comparison, the relative production of RCA product at a given concentration (RPC) was determined by setting the concentration of digested monomeric amplicon produced from CTA5 at 320 minutes to be 100. As depicted in FIG. 4, at relatively high template concentration (10 and 100 pM), the control DNA template (LB) still produced 15% and 35% of the amplicons made from CTA5. At very low template concentration (1 pM), CTA5 produced detectable amplicon in 80 minutes whereas no RCA product was observed even at 320 minutes with LB as the template.

To demonstrate the analytical utility of the selected DNA templates, a biosensing experiment was conducted where CTA5, reduced graphene oxide (rGO) and a DNA aptamer were used to achieve protein detection using a method reported previously.[19] As illustrated in FIG. 5a, this method features a rGO-adsorbed DNA probe that contains an aptamer sequence at its 5' end and a primer for RCA at its 3' end. In the presence of the cognate target, the DNA probe is released from the rGO surface, which is captured by the circular template to enable the RCA reaction for signal amplification. The well-known model thrombin-binding DNA aptamer[20] was chosen for this demonstration. The sequences of thrombin-binding probe (TP1) and circular templates (CTA5 and CDT1, a template used in the previous study that is not AC-rich) are given in FIG. 5b.

RCA reactions using 40 pM CTA5 or CDT1 was first conducted to capture TP1 that was released in the presence of 1 nM thrombin. The concentration of monomer equivalent (CME) in the RCA product produced from both CTA5 and CDT1 was determined using the digestion-dPAGE method (the data is provided in Table 4). FIG. 5c (CME vs. RCA time) clearly showed that CTA5 was more effective than CDT1.

The production of RCA product was next monitored by measuring the solution fluorescence upon addition of SYBR Gold. As expected, a higher level of fluorescence was observed with the amplicons produced with CTA5 than with CDT1. For example, ~10-fold fluorescence was observed for the RCA reaction conducted with CTA5 than with CDT1 at 1 nM thrombin (FIG. 5d). Fluorescence intensities of RCA products were also measured in response to thrombin concentrations that varied by 6 orders of magnitude (0.1-10,000 pM; FIG. 5e). The use of CTA5 can lead to the detection of 1 pM thrombin, which is ~10-fold better than the detection limit observed with CDT1 (see the insert in FIG. 5e). To the present inventor's knowledge, the 1 pM limit of detection represents the best sensitivity ever achieved with the thrombin-binding DNA aptamer.

In summary, the present inventor has developed an in vitro selection method to search for DNA sequences that can function as highly effective templates for RCA. Diverse sequences were selected with AC-richness as the common feature. The top 10 sequences, in particular, were highly rich in A and C as their average AC content surpassed 85%. To the best of the present inventor's knowledge, this finding represents a novel observation as no prior literature evidence exists for the high AC preference by phi29 DNA polymerase or other DNA polymerases. The genome of phi29 bacteriophage has a well-balanced ACGT distribution (30.1% A, 19.7% C, 20.3% G and 29.9% T) and the host bacterium, *Bacillus subtilis*, has a similar ACGT allocation (28.2% A, 21.8% C, 21.7% G and 28.3% T), and therefore, the observed AC-preference does not seem to have a biological relevance.

Without wishing to be bound by theory, the observed AC-richness may reflect phi29 DNA polymerase's propensity in handling AC-rich DNA templates (template selectivity) or utilizing dTTP and dGTP better than dATP and dCTP (nucleotide selectivity). Although the polymerase may only have a very subtle template or nucleotide selectivity for each nucleotide addition, the repetitive copying of the same template for thousands of times can significantly amplify this selectivity.

Through the study of a few AC-rich sequences with wide-ranging rankings as well as several mutants of the best performing template, strong evidence was uncovered signifying that the superior RCA efficiency of high-ranking sequences is not the property of a precise sequence but a trait reflecting their high AC content and optimal distribution of component nucleotides.

The most significant advantage offered by the selected AC-rich RCA templates is the production of more DNA amplicons at low primer/template concentrations. This benefit may allow for ultrasensitive detection involving RCA because the amplification under this scenario has to be carried out with limited amounts of the primer/template complex. Therefore the use of AC-rich templates may significantly shorten the detection time and increase the detection sensitivity. These optimal template sequences may be useful in RCA as a versatile signal amplification tool for diagnostic, biosensing and related applications.

Materials and Methods

Enzymes, Chemicals and Other Materials.

T4 DNA ligase, phi29 DNA polymerase, T4 polynucleotide kinase (PNK), EcoRV, adenosine 5'-triphosphates (ATP) and deoxynucleoside 5'-triphosphates (dNTPs) were purchased from Thermo Scientific (Ottawa, ON, Canada). SYBR Gold (10,000× concentrated stock in DMSO) was purchased from Life Technologies (Burlington, ON, Canada). [α-$^{32}$P]-dGTP was acquired from Perkin Elmer (Woodbridge, ON, Canada). Water was purified with a Milli-Q Synthesis A10 water purification system. 10×PBS (pH 7.4) was purchased from BioShop Canada (Burlington, ON. Canada), which contains 80 g/L sodium chloride, 2 g/L potassium chloride, 14.2 g/L sodium phosphate, and 2.4 g/L potassium phosphate. All other materials were purchased from Sigma-Aldrich (Oakville, ON, Canada). 2× denaturing gel loading buffer (2×GLB) was made in house with the following recipe (for 100 mL): 20 g sucrose, 10 mL of 10×TBE, 1 mL of 10% w/v SDS, 25 mg bromophenol blue, 25 mg xylene cyanole FF, and 110 g urea. The recipe for 10×TBE (1 L): 108 g Tris-base, 55 g boric acid, 20 mL of 0.5 M EDTA (pH 8.0).

Synthesis and Purification of Oligonucleotides.

DNA oligonucleotides were prepared by automated DNA synthesis using standard phosphoramidite chemistry (Integrated DNA Technologies, Coralville, Iowa, USA). The random DNA library for in vitro selection was synthesized using an equimolar mixture of the four standard phosphoramidites. All DNA oligonucleotides were purified by 10% denaturing (8 M urea) polyacrylamide gel electrophoresis (dPAGE), and their concentrations were determined spectroscopically. The DNA sequences are provided in Table 1.

Preparation of Circular DNA Templates.

Circular DNA templates were prepared from 5'-phosphorylated linear DNA oligonucleotides through template-assisted ligation with T4 DNA ligase. Each linear DNA oligonucleotide was phosphorylated as follows: a reaction mixture (50 μL) was made to contain 1 nM linear oligonucleotide, 20 U PNK (U: unit), 1×PNK buffer A (50 mM Tris-HCl, pH 7.6 at 25° C., 10 mM MgCl$_2$, 5 mM DTT, 0.1 mM spermidine), and 2 mM ATP. The mixture was incubated at 37° C. for 30 min, followed by heating at 90° C. for 5 min. The circularization reaction was conducted in a volume of 400 μL, produced by adding 306 μL of H$_2$O and 2 μL of a DNA template (DT1 or DT2, 500 pM) to the phosphorylation reaction mixture above. After heating at 90° C. for 3 min and cooling down at room temperature (RT) for 10 min, 40 μL of 10×T4 DNA ligase buffer (400 mM Tris-HCl, 100 mM MgCl$_2$, 100 mM DTT, 5 mM ATP, pH 7.8 at 25° C.) and 2 μL of T4 DNA ligase (5 U/μL) were added. This mixture was incubated at RT for 2 h before heating at 90° C. for 5 min to deactivate the ligase. The ligated circular DNA molecules were concentrated by standard ethanol precipitation and purified by 10% dPAGE. The concentration of the circular DNA template was determined spectroscopically.

In Vitro Selection Protocol.

The DNA library, denoted DL1, contained 60 nucleotides (nt) distributed into a central random-sequence domain of 35 nt and two constant regions, 15 nt at the 5' end and 10 nt at 3' ends. Its sequence is provided in Table 1. After circularization in the presence of DT1 using the protocol described above, the circular template, denoted CTA, was purified by 10% dPAGE. Note that CTA contains a recognition site for the restriction enzyme EcoRV (shown in italic-bold in Table 1). The RCA for the first round of selection was performed in 50 μL of 1×RCA buffer (made from 10× stock, which is made of 330 mM Tris-acetate, pH 7.9 at 37° C., 100 mM magnesium acetate, 660 mM potassium acetate, 1% (v/v) Tween 20, 10 mM DTT) containing 2 μM CTA (100 pmol), 2 μM DT1 (100 pmol), 1 mCi [α-$^{32}$P]-dGTP, 0.7 mM dGTP (35 nmol), 1 mM dATP, dTTP and dCTP (50 nmol each). After heating at 90° C. for 3 min, the solution was cooled to room temperature for 10 min. Subsequently, 0.5 μL of phi29 DNA polymerase (10 U/μL) was added, followed by incubation at 30° C. for 20 min. Finally, the mixture was heated to 65° C. for 10 min to deactivate the polymerase.

To the RCA reaction mixture above, 2 μL of 500 μM DT2 (1 nmol) was introduced. The mixture was heated at 90° C. for 3 min and cooled at RT for 10 min, followed by the addition of 10 μL of 10× Fast Digestion Buffer (100 mM Tris-HCl, pH 8.0, 50 mM MgCl$_2$, 1 M NaCl, 1 mg/mL BSA) and 5 μL of FastDigest EcoRV (unit size 400 reactions; the total volume is 400 μL). The total reaction volume was increased to 100 μL. The reaction mixture was then incubated at 37° C. for 16 h. The restriction enzyme was inactivated at 65° C. for 10 min. The monomerized RCA products were concentrated by standard ethanol precipitation and purified by dPAGE. The DNA was then eluted and circularized into circular DNA template B (CTB), which was used for the second RCA reaction. The reaction condition was identical to the first RCA except for the replacement of DT1 with DT2. For the restriction digestion after RCA, DT2 was replaced DT1.

Seven rounds of selection were conducted while the amount of the circular template was reduced from 100 pmol (round 1) to 10 pmol (round 2), 1 pmol (rounds 3-5), and 0.1 pmol (rounds 6 and 7), which was used as a strategy to favor the selection of highly efficient DNA templates. DNA pool from the $7^{th}$ round was used for deep sequencing as described next.

Sequencing Protocol.

CTA, CTB in round 7 and LB, was digested into linear DNA sequences as previously described. 2 µL of 0.05 µM linear CTA, CTB and LB were amplified by PCR. There were two PCR steps. In PCR1, a reaction mixture (50 µL) was prepared to contain the DNA above, 0.4 µM each of forward primer (FP) and reverse primer (RP; their sequences are provided in Table 1), 200 µM each of dNTPs (dATP, dCTP, dGTP and dTTP), 1×PCR buffer (75 mM Tris-HCl, pH 9.0, 2 mM MgCl$_2$, 50 mM KCl, 20 mM (NH4)$_2$SO$_4$) and 1.5 U Taq DNA polymerase. The DNA was amplified using the following thermocycling steps: 94° C. for 3 min; 15 circles of 94° C. (30 s), 42° C. (45 s) and 72° C. (45 s); 72° C. for 1 min. 1 µL of the PCR1 product was diluted with H$_2$O to 100 µL, 2 µL of which was used as the template for PCR2 using deep sequencing primers DF and DR (their sequences are provided in Table 1) while following the same protocol above for PCR1 except that the annealing temperature increased to 48° C. Note that the numbers of amplification cycles between CTA, CTB and LB were adjusted, typically between 12 and 15 cycles. The DNA product generated in PCR2 was analyzed by 2% agarose gel electrophoresis and sent out for deep sequencing. Paired-end next generation sequencing (NGS) was done using an Illumina Miseq system at the Farncombe Metagenomics Facility, McMaster University. Forward and reverse reads were sorted by tag and exported as FASTQ files using the Illumina Basespace platform. Primer domains were removed and paired-end reads were merged using PANDAseq 2.6, only sequences possessing perfect complementarity between paired-end reads were output in FASTA format for further analysis (Ref. 1). Sequences were dereplicated and tagged with copy number using USEARCH v7.0.1090_i86linux32 sequence analysis package (Ref. 2). USEARCH was also used for clustering of dereplicated populations using the -cluster_smallmem command at 0.9 identity threshold. PANDAseq and USEARCH software packages were run on Ubuntu Linux 12.04 LTS. Analysis of sequence populations, rankings and base composition were done using Microsoft Excel 2010 running on a Windows 8 PC.

Figure 2:
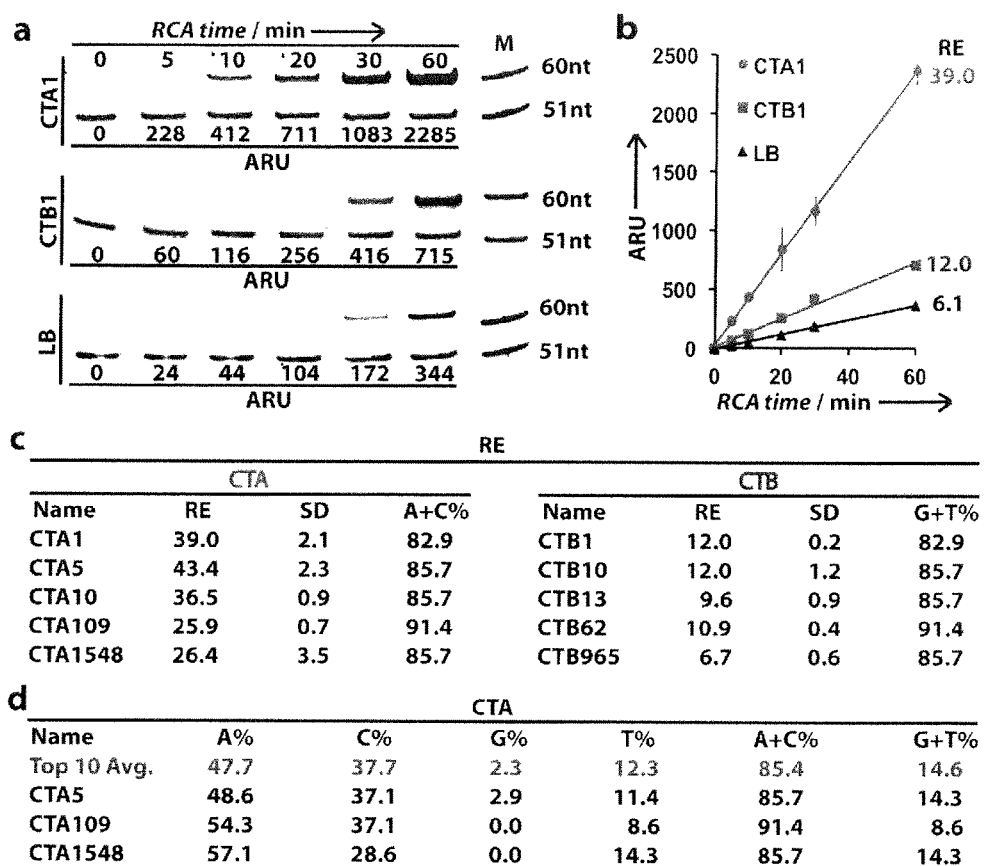
FIG. 2 shows determination of RCA efficiency (RE) of selective CTAs and CTBs in an embodiment of the application. (a) dPAGE analysis of digested RCA products obtained from varying time of RCA with CTA1, CTB1, and LB. The top band: digested RCA monomer (60 nt); the bottom band: DNA loading control (51 nt). ARU: average repeating units of the RCA product from a given circular template. (b) ARU vs. RCA time for CTA1, CTB1 and LB. (c) RE values of 5 CTA/CTB pairs. ARU values that were used to derive RE values are provided in Table 2. SD: standard deviation. (d) Percent ACGT in CTA5, CTA109 aid CTA1548.

Experimental Details for FIGS. 2 and 3:

RCA Reaction.

The RCA reaction was performed in 50 µL. 2 µL of a relevant, 0.01 µM circular DNA template (the final concentration=0.4 nM) was mixed with 2 µL of 50 µM DT1 (used for CTAs and LB) or DT2 (used for CTBs; the final DT1 or DT2 concentration=2 µM), 5 µL of 10 mM each of dGTP, dATP, dTTP and dCTP (the final concentration=1 mM each), 5 µL 10×RCA buffer and 35.5 µL of H$_2$O. After heating at 90° C. for 3 min, the solution was cooled to room temperature for 10 min. 0.5 µL of 10 U/µL phi29 DNA polymerase was then added, followed by incubation at 30° C. for 5, 10, 20, 30 and 60 min. This mixture was heated to 65° C. for 10 min to deactivate the polymerase.

Restriction Digestion.

The digestion reaction was performed in 10 µL. A 5-µL aliquot of the above RCA reaction mixture was combined with 2 µL of 50 µM DT2 (used for CTAs and LB) or CT1 (used for CTBs; the final DT1 or DT2 concentration=10 µM), heated at 90° C. for 3 min and cooled at RT for 10 min. This was followed by the addition of 1 µL of 10× Fast Digestion Buffer and 2 µL of FastDigest EcoRV. The reaction mixture was then incubated at 37° C. for 16 h.

Analysis of Monomeric RCA Products.

The above digestion mixture was combined with 10 µL of 2× denaturing gel loading buffer (2×GLB), and 4 µL of 200 nM DLC (in 1×GLB; the final concentration=33.3 nM); its sequence is provided in Table 1). The final volume of this DNA mixture was 24 µL. A 5-µL aliquot was then run on a 10% dPAGE gel. After electrophoresis, the gel was stained with 1×SYBR Gold (diluted from the 10,000× concentrated stock solution). A fluorescent image of the stained gel was obtained using Typhoon 9200 and analyzed using Image Quant software (Molecular Dynamics).

Calculation of FR, $C_M$, $C_{ME}$, and ARU.

The fluorescence intensity of the 60-nt monomeric DNA band ($F_{60nt}$) and the 51-nt DLC band ($F_{51nt}$) from each digestion mixture was calculated and used to derive an FR (fluorescence ratio) value using Equation 1:

$$FR = F_{60nt}/F_{51nt} \qquad \text{Eq. 1}$$

The FR value is used to calculate the concentration of the monomer, $C_M$, of the digestion mixture using equation 2:

$$C_M = FR \times 33.3 \text{ nM} \times 2.4 \qquad \text{Eq. 2}$$

Note that 2.4 is the volume correction factor, which is calculated from 24/10 (the final volume of the digested monomer-DLC mixture was 24 µL whereas the volume of the digestion reaction mixture was 10 µL). The $C_M$ values are further used to calculate the concentration of monomer equivalent ($C_{ME}$) in the RCA product in the RCA reaction mixture using Equation 3:

$$C_{ME} = C_M \times 2 \qquad \text{Eq. 3}$$

Note that 2 is the volume correction factor, which is calculated from 10/5 (5 µL of the RCA reaction mixture were used to produce 10 µL of the digestion reaction mixture). $C_{ME}$ can also be calculated from FR using Equation 4.

$$C_{ME} = FR \times 33.3 \text{ nM} \times 2.4 \times 2 = FR \times 159.8 \text{ nM} \qquad \text{Eq. 4}$$

Since the concentration of each circular template, [CT] (in nM), was the limiting factor of the RCA reaction, the average repeating units (ARU) of the RCA product can be estimated using Equation 5:

$$ARU = FR/[CT] \times 159.8 \qquad \text{Eq. 5}$$

The calculated ARU values for all the RCA reactions (performed twice) featured in FIGS. 2 and 3 are summarized in Table 2.

Experimental Details for FIG. 4.

RCA Reaction.

The RCA reactions were carried in the same way as described in the experimental details for FIGS. 2 and 3, with the following exceptions: (1) two circular templates, CTA5 and LB, were examined for RCA at the template concentration of 0.001, 0.01, and 0.1 nM; (2) each RCA reaction was carried out for 5, 10, 20, 40, 80, 160 and 320 min.

Restriction Digestion and Analysis of Monomeric RCA Products.

Both were carried out identically as described in the experimental details for FIGS. 2 and 4 except for the following: a 4-µL aliquot of the RCA reaction mixture (instead of 5 µL) was used to set up the digestion reaction.

Calculation of FR, $C_M$, RPC.

FR and $C_M$ were calculated using Equations 1 and 2. Table 3 lists $C_M$ values for each reaction time at each template concentration, which were used to calculate the relative production of RCA product at a given concentration (RPC) using Equation 6.

$$RPC = 100 \times C_{M,t}/C_{M,320M} \qquad \text{Eq. 6}$$

$C_{M, t}$ is the concentration of digested RCA product of CTA5 or LB at time t and $C_{M, 320M}$ is the concentration produced from CTA5 at 320 min.

Figure 5:
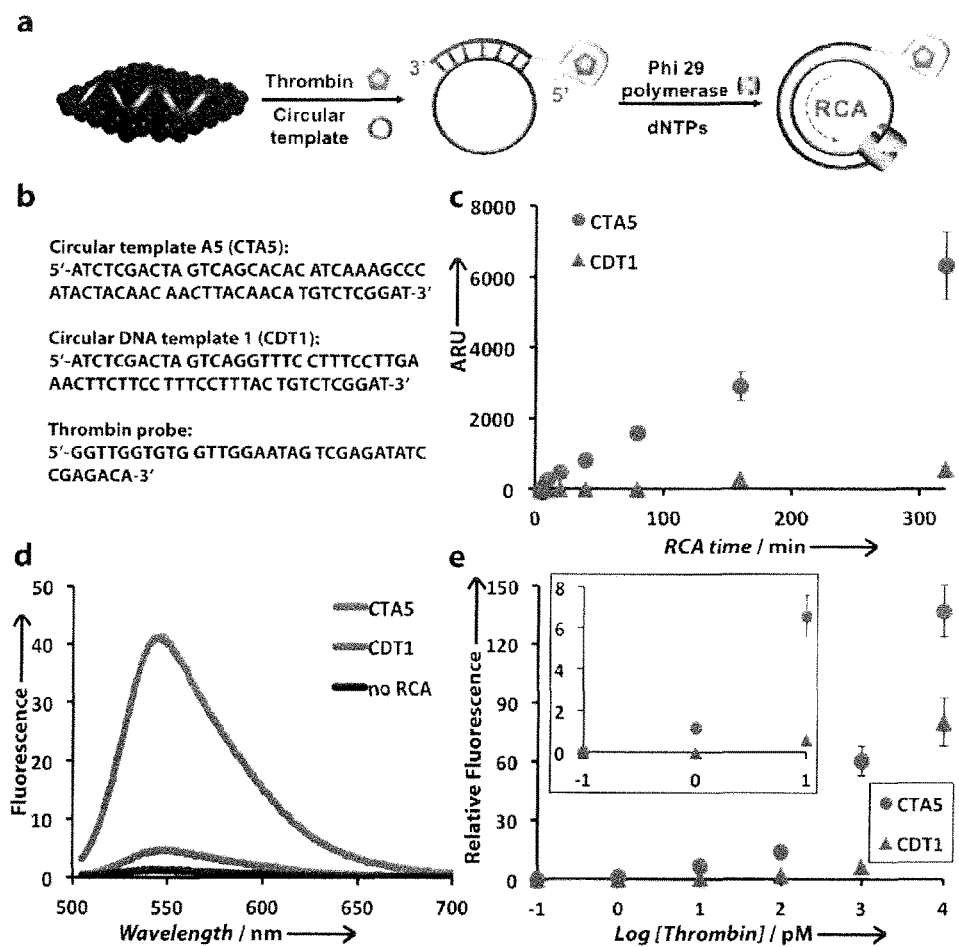
FIG. 5 shows thrombin detection using CTA5-assisted RCA in an exemplary embodiment of the application. (a) Detection strategy. (b) The sequences of circular templates (SEQ ID NO:16 and 30, respectively) and the aptamer probe (SEQ ID NO:31). (c) Comparison of time-dependent amplicon formation from CTA5 and CDT1. (d) Fluorescence spectra of SYBR Gold-RCA product mixtures obtained with CTA5 and CDT1. (e) Relative fluorescence (RF) vs. thrombin concentration. RF=F/Fc, where F is the fluorescence of a given mixture and Fc is the fluorescence of the no RCA control. The RCA time for d and e is 60 min.

Experimental Details for FIG. 5.

Preparation of Reduced Graphene Oxide.

Graphene oxide (GO) was prepared according to a previously reported modified Hummers method (Ref. 3). To produce reduced graphene oxide (rGO), an aqueous solution containing 1 mL of 0.1 mg/mL GO, 10 µL of 10 mg/mL L-ascorbic acid and 2 µL of ammonia solution was heated at 90° C. for 5 min. After that, the mixture was cooled to room temperature and the stably dispersed rGO solution was obtained.

DNA Probe Adsorption by rGO.

450 µL of target binding buffer (TBB; 20 mM PBS, 150 mM NaCl, 20 mM KCl, 5 mM MgCl₂, pH 7.5), 10 µL of 15 µM thrombin-binding DNA probe (TP1), and 40 µL of 100 µg/mL rGO solution were incubated at 30° C. for 30 min. The final TP1 concentration thus was 300 nM whereas the final rGO concentration was 8 µg/mL. Under this condition, the DNA probe is completely adsorbed by rGO (Ref. 4).

DNA Probe Release by Thrombin.

48 µL of the TP1-rGO mixture was transferred into a 1.5-mL microcentrifuge tube, and combined with 2 µL of a thrombin stock solution with a defined concentration of thrombin. The reaction mixture was incubated at 30° C. for 30 min, then centrifuged for 10 min at 15,000 g to remove the rGO. The supernatant was used for RCA reactions as described below.

Experimental Details for FIG. 5c.

The RCA reactions were carried out in the same way as described in the experimental procedure for FIGS. 2 and 4, with the following exceptions: (1) two circular templates, CTA5 and CDT1, were examined for RCA at the template concentration of 0.04 nM and 5 µL of TP1 solution released by 1 nM thrombin; (2) each RCA reaction was carried out for 5, 10, 20, 40, 80, 160 and 320 min. Restriction digestion and analysis of monomeric RCA products were carried out identically as described for FIGS. 2 and 4 except for the following: a 4-µL aliquot of the RCA reaction mixture (instead of 5 µL) was used to set up the digestion reaction. FR and $C_M$ were calculated using Equations 1 and 2; however $C_{ME}$ values were calculated using Equation 7, owing to the use of 4 µL (rather than 5 µL) of the RCA reaction mixture to set up the 10-µL digestion reaction (the volume correction factor thus becomes 2.5).

$$C_{ME} = FR \times 33.3 \text{ nM} \times 2.4 \times 2.5 = FR \times 199.8 \text{ nM} \qquad \text{Eq. 7}$$

The calculated $C_{ME}$ values for all the RCA reactions featured in FIG. 5c are summarized in Table 4.

Experimental Details for FIG. 5d.

The RCA reactions were carried in the same way as described in the experimental procedure for FIGS. 2 and 4, with the following exceptions: (1) two circular templates, CTA5 and CDT1, were examined for RCA at the template concentration of 0.4 nM and 5 µL of TP1 solution released by 1,000 pM thrombin; (2) each RCA reaction was carried out for 60 min; (3) two no-RCA control reactions were also carried out for both CTA5 and CDT1 and these reactions contained the same RCA components except phi29 DNA polymerase. Following the RCA reaction, the fluorescence measurement was carried out as follows: 7 µL of the RCA reaction mixture was mixed with 6 µL of 10×SYBR Gold (diluted from the 10,000× concentrated stock), 6 µL of 10×TBE and 41 µL of H₂O. Note that the reaction tube was wrapped with aluminum foil to prevent photo-bleaching. The mixture was incubated at RT for 5 min and the fluorescence spectrum (Aem=500-700 nm) was obtained using a Cary Eclipse fluorescence spectrophotometer (Varian) with an excitation wavelength (λex) at 495 nm. The bandpasses for excitation and emission were both set at 5 nm.

Experimental Details for FIG. 5e.

The experimental procedure for this panel was identical to that used for panel 5d except that several more RCA reactions were performed using the TP1 solution released by 0.1, 1, 10, 100, 1,000 and 10,000 pM thrombin. The fluorescence intensity at the maximal emission wavelength (λ=545 nm) was obtained for each test solution and used to calculate the relative fluorescence using Equation 8:

$$RF = (F_T - F_C)/F_C \qquad \text{Eq. 8}$$

$F_T$: fluorescence reading of a test RCA-SYBR Gold mixture; $F_C$: fluorescence reading of the control RCA-SYBR Gold mixture. RF vs. the original thrombin concentration is plotted as FIG. 5e.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

DNA oligonucleotides used

| Name | Sequence (5'-3') |
|---|---|
| DL1 (LB) | ATCTCGACTA GTCAG-N₃₅- TGTCTCGGAT (SEQ ID NO: 11) |
| DT1 | TAGTCGAGAT ATCCGAGACA (SEQ ID NO: 12) |
| DT2 | TGTCTCGGAT ATCTCGACTA (SEQ ID NO: 13) |
| DLC | TTCGGAAGAG ATGGCGACGC CGAACTATCT CTCGAGCTGA TCCTGATGGA A (SEQ ID NO: 14) |
| CTA1 | ATCTCGACTA GTCAGAACAA TACCCATCAA GCACCAACCA CATTTCACAC TGTCTCGGAT (SEQ ID NO: 15) |
| CTA5 | ATCTCGACTA GTCAGCACAC ATCAAAGCCC ATACTACAAC AACTACAACA TGTCTCGGAT (SEQ ID NO: 16) |
| CTA10 | ATCTCGACTA GTCAGAAGAA CAAACACTTC CCCATACCAC ACAACATCAA TGTCTCGGAT (SEQ ID NO: 17) |
| CTA109 | ATCTCGACTA GTCAGCACAT ACAACACACA AATCACCAAC AACACAACAT TGTCTCGGAT (SEQ ID NO: 18) |
| CTA1548 | ATCTCGACTA GTCAGAATAA TCAAACAACA CCACAACTAT CAAAATACCA TGTCTCGGAT (SEQ ID NO: 19) |
| CTB1 | ATCCGAGACA GTGTGAAATG TGGTTGGTGC TTGATGGGTA TTGTTCTGAC TAGTCGAGAT (SEQ ID NO: 20) |

TABLE 1-continued

DNA oligonucleotides used

| Name | Sequence (5'-3') |
|---|---|
| CTB10 | ATCCGAGACA TGTTGTAGTT GTTGTAGTAT GGGCTTTGAT GTGTGCTGAC TAGTCGAGAT (SEQ ID NO: 21) |
| CTB13 | ATCCGAGACA TTGATGTTGT GTGGTATGGG GAAGTGTTTG TTCTTCTGAC TAGTCGAGAT (SEQ ID NO: 22) |
| CTB62 | ATCCGAGACA ATGTTGTGTT GTTGGTGATT TGTGTGTTGT ATGTGCTGAC TAGTCGAGAT (SEQ ID NO: 23) |
| CTB965 | ATCCGAGACA TGGTATTTTG ATAGTTGTGG TGTTGTTTGA TTATTCTGAC TAGTCGAGAT (SEQ ID NO: 24) |
| CTA5M1 | ATCTCGACTA GTCAGACAAC ATCAAAGCCC ATACTCACAC AACTACAACA TGTCTCGGAT (SEQ ID NO: 25) |
| CTA5M2 | ATCTCGACTA GTCAGCACAC AACTAAGCCC ATACTACAAC ATCAACAACA TGTCTCGGAT (SEQ ID NO: 26) |
| CTA5M3 | ATCTCGACTA GTCAGCACAC ATCAACAACA ATACTACAAC AACTAAGCCC TGTCTCGGAT (SEQ ID NO: 27) |
| CTA5M4 | ATCTCGACTA GTCAGATACT ATCAAAGCCC CACACACAAC AACTACAACA TGTCTCGGAT (SEQ ID NO: 28) |
| CTA5M5 | ATCTCGACTA GTCAGCAAAA ACATGTCAAC CCAACAAACC ATCCACTCAA TGTCTCGGAT (SEQ ID NO: 29) |
| CDT1 | ATCTCGACTA GTCAGGTTTC CTTTCCTTGA AACTTCTTCC TTTCCTTTAC TGTCTCGGAT (SEQ ID NO: 30) |
| TP1 | GGTTGGTGTG GTTGGAATAG TCGAGATATC CGAGACA (SEQ ID NO: 31) |
| FP | GCCTCAACTT ATCCGAGACA (SEQ ID NO: 32) |
| RP | ATCTCGACTA GTCAGGCACT (SEQ ID NO: 33) |
| DF | AATGATACGG CGACCACCGA GATCTACACT CTTTCCCTAC ACGACGCTCT TCCGATCTGC CTCAACTTAT CCGAGACA (SEQ ID NO: 34) |
| DR | CAAGCAGAAG ACGGCATACG AGATTTCTTG GTGACTGGAG TTCAGACGTG TGCTCTTCCG ATCTATCTCG ACTAGTCAGG CACT (SEQ ID NO: 35) |

TABLE 2

ARU values for FIGS. 2 and 3

| Name | Repeat | RCA5M | RCA10M | RCA20M | RCA30M | RCA60M |
|---|---|---|---|---|---|---|
| CTA1 | 1 | 227.7 | 411.5 | 711.1 | 1082.6 | 2285.1 |
|  | 2 | 239.7 | 455.4 | 970.8 | 1250.4 | 2452.9 |
| CTA5 | 1 | 254.8 | 456.8 | 791.9 | 1204.1 | 2540.4 |
|  | 2 | 267.3 | 508.5 | 1080.8 | 1390.8 | 2725.3 |
| CTA10 | 1 | 174.1 | 377.6 | 735.4 | 1167.8 | 2132.9 |
|  | 2 | 164.8 | 340.0 | 671.2 | 1089.6 | 2212.5 |
| CTA109 | 1 | 247.7 | 379.8 | 731.8 | 859.0 | 1648.7 |
|  | 2 | 196.0 | 383.9 | 705.4 | 994.7 | 1539.2 |
| CTA1548 | 1 | 210.2 | 361.2 | 622.3 | 996.8 | 1749.2 |
|  | 2 | 202.0 | 352.3 | 669.1 | 906.5 | 1459.4 |
| CTB1 | 1 | 59.9 | 115.9 | 255.7 | 415.5 | 715.1 |
|  | 2 | 67.9 | 127.8 | 251.7 | 431.5 | 695.1 |
| CTB10 | 1 | 49.8 | 93.9 | 195.0 | 388.4 | 752.0 |
|  | 2 | 40.8 | 82.5 | 169.0 | 336.6 | 651.7 |
| CTB13 | 1 | 73.5 | 128.8 | 259.8 | 313.5 | 627.2 |
|  | 2 | 71.2 | 106.9 | 221.1 | 294.4 | 542.4 |
| CTB62 | 1 | 54.5 | 87.7 | 203.0 | 325.6 | 631.7 |
|  | 2 | 50.5 | 80.9 | 210.0 | 368.2 | 648.0 |
| CTB965 | 1 | 32.9 | 64.0 | 117.4 | 178.6 | 373.9 |
|  | 2 | 43.4 | 65.2 | 140.2 | 217.2 | 429.1 |
| CTA5M1 | 1 | 175.7 | 309.7 | 564.5 | 1055.7 | 2086.1 |
|  | 2 | 182.5 | 339.3 | 707.3 | 1298.3 | 2181.2 |
| CTA5M2 | 1 | 173.2 | 303.4 | 544.2 | 979.5 | 1872.9 |
|  | 2 | 177.8 | 359.1 | 594.1 | 1075.7 | 2119.1 |
| CTA5M3 | 1 | 218.8 | 359.4 | 763.9 | 1264.5 | 2279.5 |
|  | 2 | 290.1 | 542.4 | 1097.5 | 1432.5 | 2468.3 |
| CTA5M4 | 1 | 264.2 | 477.8 | 964.8 | 1500.7 | 2520.6 |
|  | 2 | 197.4 | 360.3 | 704.1 | 1200.7 | 2374.6 |
| CTA5M5 | 1 | 231.2 | 480.4 | 850.0 | 1298.4 | 2398.1 |
|  | 2 | 164.3 | 404.7 | 985.1 | 1278.8 | 2444.4 |
| LB | 1 | 24.0 | 55.9 | 123.8 | 203.7 | 379.5 |
|  | 2 | 24.0 | 43.9 | 103.9 | 171.8 | 343.6 |

TABLE 3

$C_M$ value for each reaction time at each template concentration

| Name | Repeat | $C_{M,5M}$ | $C_{M,10M}$ | $C_{M,20M}$ | $C_{M,40M}$ | $C_{M,80M}$ | $C_{M,160M}$ | $C_{M,320M}$ |
|---|---|---|---|---|---|---|---|---|
| CTA5 - 0.001 nM | 1 | 0 | 0 | 0 | 0 | 3.7 | 7.2 | 16.1 |
|  | 2 | 0 | 0 | 0 | 0 | 4.4 | 9.5 | 18.0 |
| CTA5 - 0.01 nM | 1 | 0 | 5.7 | 8.6 | 19.0 | 45.4 | 106.5 | 187.6 |
|  | 2 | 0 | 5.4 | 11.0 | 18.0 | 40.5 | 83.9 | 166.5 |
| CTA5 - 0.1 nM | 1 | 17.7 | 34.0 | 65.9 | 129.3 | 252.1 | 408.3 | 530.5 |
|  | 2 | 15.9 | 31.3 | 70.1 | 125.4 | 243.9 | 419.4 | 502.6 |
| LB - 0.001 nM | 1 | 0 | 0 | 0 | 0 | 0 | 0 | 0 |
|  | 2 | 0 | 0 | 0 | 0 | 0 | 0 | 0 |
| LB - 0.01 nM | 1 | 0 | 0 | 0 | 3.2 | 6.4 | 15.5 | 28.2 |
|  | 2 | 0 | 0 | 0 | 4.0 | 6.0 | 12.0 | 24.5 |
| LB - 0.1 nM | 1 | 3.5 | 6.4 | 14.1 | 32.9 | 62.8 | 119.4 | 194.1 |
|  | 2 | 3.2 | 6.1 | 15.7 | 32.2 | 67.1 | 113.3 | 173.8 |

TABLE 4

$C_{ME}$ values for FIG. 5c

| Name | Rpt | RCA5M | RCA10M | RCA20M | RCA40M | RCA80M | RCA160M | RCA320M |
|---|---|---|---|---|---|---|---|---|
| CTA5 | 1 | 0 | 11.1 | 20.1 | 35.9 | 68.9 | 127.2 | 278.5 |
|  | 2 | 0 | 9.6 | 17.9 | 28.8 | 57.7 | 104.3 | 225.1 |
| CDT1 | 1 | 0 | 0 | 0 | 0 | 0 | 13.8 | 10.1 |
|  | 2 | 0 | 0 | 0 | 0 | 0 | 24.2 | 19.8 |

REFERENCES

Ref. 1: A. P. Masella, A. K. Bartram, J. M. Truszkowski, D. G. Brown, J. D. Neufeld, *BMC Bioinformatics* 2012, 13, 31.

Ref. 2: R. C. Edgar, *Bioinformatics* 2010, 26, 2460-2461.

Ref 3: M. Liu, H. M. Zhao, S. Chen, H. Yu, X. Quan, *ACS Nano* 2012, 6, 3142-3151.

Ref. 4: M. Liu, J. Song, S. Shuang, C. Dong, J. D. Brennan, Y. Li, *ACS Nano* 2014, 8, 5564-5573.

[1] a) A. Fire, S. Q. Xu, *Proc. Natl. Acad. Sci. USA* 1995, 92, 4641-4645; b) D. Liu, S. L. Daubendiek, M. A. Ziliman, K. Ryan, E. T. Kool, *J. Am. Chem. Soc.* 1996, 118, 1587-1594.

[2] a) M. Nilsson, F. Dahl, C. Larsson, M. Gullberg, J. Stenberg, *Trends Biotechnol.* 2006, 24, 83-88; b) W. Zhao, M. M. Ali, M. A. Brook, Y. Li, *Angew. Chem. Int. Ed.* 2008, 47, 6330-6337; c) M. M. Ali, F. Li, Z. Zhang, K. Zhang, D. K. Kang, J. A. Ankrum, X. C. Le, W. Zhao, *Chem. Soc. Rev.* 2014, 43, 3324-3341; d) F. Wang, C. Lu, I. Willner, *Chem. Rev.* 2014, 114, 2881-2941.

[3] a) L. Blanco, A. Bernad, J. M. Lazaro, G. Martin, C. Garmendia, M. Salas, *J. Biol. Chem.* 1989, 264, 8935-8940; b) D. Canceill, E. Viguera, S. D. Ehrlich, *J. Biol. Chem.* 1999, 274, 27481-27490.

[4] a) S. Kamtekar, A. J. Berman, J. Wang, J. M. Lazaro, M. de Vega, L. Blanco, M. Salas, T. A. Steitz, *Mol. Cell.* 2004, 16, 609-618; b) J. A. Morin, F. J. Cao, J. M. Lazaro, J. R. Arias-Gonzalez, J. M. Valpuesta, J. L. Carrascosa, M. Salas, B. Ibarra, *Proc. Natl. Acad. Sci. USA* 2012, 109, 8115-8120; c) M. Salas, *J. Biol. Chem.* 2012, 287, 44568-44579.

[5] a) C. Larsson, J. Koch, A. Nygren, G. Janssen, A. K. Raap, U. Landegren, Nilsson, *Nat. Methods* 2004, 1, 227-232; b) Y. Liu, H. Yao, J. Zhu, *J. Am. Chem. Soc.* 2013, 135, 16268-16271; c) C. Lin, Y. Zhang, X. Zhou, B. Yao, Q. Fang, *Biosens. Bioelectron.* 2013, 47, 515-519; d) Z. S. Wu, Z. Shen, K. Tram, Y. Li, *Nat. Commun.* 2014, 5, 4279; e) C. Russell, K. Welch, J. Jarvius, Y. Cai, R. Brucas, F. Nikolajeff, P. Svedlindh, M. Nilsson, *ACS Nano,* 2014, 8, 1147-1153.

[6] a) Y. Weizmann, M. K. Beissenhirtz, Z. Cheglakov, R. Nowarski, M. Kotler, I. Willner, *Angew. Chem. Int. Ed.* 2006, 45, 7384-7388; b) Y. Tian, Y. He, C. Mao, *ChemBioChem* 2006, 7, 1862-1864; c) Z. Cheglakov, Y. Weizmann, B. Basnar, I. Willner, *Org. Biomol. Chem.* 2007, 5, 223-225; d) F. Wang, C. Lu, X. Liu, L. Freage, I. Willner, *Anal. Chem.* 2014, 86, 1614-1621.

[7] a) C. Larsson, I. Grundberg, O. Soderberg, M. Nilsson, *Nat. Methods.* 2010, 7, 395-397; b) Y. Zhou, Q. Huang, J. Gao, J. Lu, X. Shen, C. Fan, *Nucleic Acids Res.* 2010, 38, e156; c) E. M. Harcourt, E. T. Kool, *Nucleic Acids Res.* 2012, 40, e65; d) Y. Wen, Y. Xu, X. Mao, Y. Wei, H. Song, N. Chen, Q. Huang, C. Fan, D. Li, *Anal. Chem.* 2012, 84, 7664-7669.

[8] a) H. Liu, L. Li, L. Duan, X. Wang, Y. Xie, L. Tong, Q. Wang, B. Tang, *Anal. Chem.* 2013, 85, 7941-7947; b) Y. Li, L. Liang, C. Zhang, *Anal. Chem.* 2013, 85, 11174-11179; c) R. Deng, L. Tang, Q. Tian, Y. Wang, L. Lin, J. Li, *Angew. Chem. Int. Ed.* 2014, 53, 2389-2393; d) J. Ge, L. L. Zhang, S. J. Liu, R. Q. Yu, Chu X. *Anal. Chem.* 2014, 86, 1808-1815.

[9] a) D. A. Di Giusto, W. A. Wlassoff, J. J. Gooding, B. A. Messerle, G. C. King, *Nucleic Acids Res.* 2005, 33, e64; b) L. Yang, C. W. Fung, E. J. Cho, A. D. Ellington, *Anal. Chem.* 2007, 79, 3320-3329; c) L. Zhou, L. J. Ou, X. Chu, G. L. Shen, R. Q. Yu, *Anal. Chem.* 2007, 79, 7492-7500;

[10] a) W. Zhao, C. H. Cui, S. Bose, D. Guo, C. Shen, W. P. Wong, K. Halvorsen, O. C. Farokhzad, G. S. L. Teo, J. A. Phillips, *Proc. Nat. Acad. Sci. USA* 2012, 109, 19626-19631; C. Ding, H. Liu, N. Wang, Z. Wang, *Chem. Comm.* 2012, 48, 5019-5021; c) L. Wang, K. Tram, M. M. Ali, B. J. Salena, J. Li, Y. Li, *Chem. Eur. J.* 2014, 20, 2420-2424; d) P. He, Q. Qiao, L. Liu, S. Zhang, *Chem. Comm.* 2014, 50, 10718-10721.

[11] a) E. J. Cho, L. Yang, M. Levy, A. D. Ellington, *J. Am. Chem. Soc.* 2005, 127, 2022-2023; b) M. M. Ali, Y. Li, *Angew. Chem. Int. Ed.* 2009, 48, 3512-3515; c) L. Tang, Y. Liu, M. M. Ali, D. K. Kang, W. Zhao, J. Li, *Anal. Chem.* 2012, 84, 4711-4717; d) S. A. McManus, Y. Li, *J. Am. Chem. Soc.* 2013, 135, 7181-7186.
[12] a) G. F. Joyce, *Annu. Rev. Biochem.* 2004, 73, 791-836; b) G. Mayer, *Angew. Chem. Int. Ed.* 2009, 48, 2672-2689; c) M. Famulok, G. Mayer, *Chem. Biol.* 2014, 21, 1055-1058.
[13] a) R. R. Breaker, G. F. Joyce, *Chem. Biol.* 1994, 1, 223-229; b) S. W. Santoro, G. F. Joyce, *Proc. Natl. Acad. Sci. USA* 1997, 94, 4262-4266; c) A. Barley, D. Sen, *J. Am. Chem. Soc.* 2013, 135, 2596-2603; d) B. M. Brandsen, T. E. Velez, A. Sachdeva, N. A. Ibrahim, S. K. Silverman, *Angew. Chem. Int. Ed.* 2014, 53, 9045-9050.
[14] a) Y. Xiang, Y. Lu, *Nat. Chem.* 2011, 3, 697-703; b) P. J. Huang, J. Liu, *Anal. Chem.* 2014, 86, 5999-6005; c), K. Hwang, P. Wu, T. Kim, L. Lei, S. Tian, Y. Wang, Y. Lu, *Angew. Chem. Int. Ed.* 2014, 53, 13798-13802; d) K. Tram, P. Kanda, B. J. Salena, S. Huan, Y. Li, *Angew. Chem. Int. Ed.* 2014, 53, 12799-12802.
[15] a) K. Schlosser, Y. Li, *Chem. Biol.* 2009, 16, 311-322; b) S. K. Silverman, *Angew. Chem. Int. Ed.* 2010, 49, 7180-7201; c) R. R. Breaker, G. F. Joyce, *Chem. Biol.* 2014, 21, 1059-1065.
[16] a) N. K. Navani, Y. Li, *Curr. Opin. Chem. Biol.* 2006, 10, 272-281; b) J. Liu, Z. Cao, Y. Lu, *Chem. Rev.* 2009, 109, 1948-1998; c) H. Q. Zhang, F. Li, H. Q. Zhang, F. Li, B. Dever, X. F. Li, X. C. Le, *Chem. Rev.* 2013, 113, 2812-2841.
[18] a) A. D. Ellington, J. W. Szostak, *Nature* 1990, 346, 818-822; b) C. Tuerk, L. Gold, *Science* 1990, 249, 505-510.
[19] M. Liu, J. Song, S. Shuang, C. Dong, J. D. Brennan, Y. Li, *ACS Nano* 2014, 8, 5564-5573.
[20] L. C. Bock, L. C. Griffin, J. A. Latham, E. H. Vermaas, J. J. Toole, *Nature* 1992, 355, 564-566.

The invention claimed is:

1. A biosensor comprising:
   a) reduced graphene oxide (rGO); and
   b) a nucleic acid probe absorbed on the rGO, the nucleic acid probe comprising an RCA primer sequence linked to a recognition moiety for an analyte.

2. The biosensor of claim 1, wherein the recognition moiety is an aptamer that changes conformation in presence of the analyte, a DNAzyme that cleaves RNA in the presence of the analyte, or an antibody.

3. The biosensor of claim 2, wherein the aptamer recognition moiety changes conformation after binding to the analyte and the nucleic acid probe desorbs from the rGO.

4. The biosensor of claim 1, wherein the analyte is a nucleic acid, protein or small molecule.

5. The biosensor of claim 1, wherein the recognition moiety for the analyte is at the 5' end of the probe and the RCA primer sequence is at the 3' end of the probe.

6. A kit for detection of an analyte comprising (i) the biosensor of claim 1; (ii) a circular template comprising a sequence that is complementary to the RCA primer sequence; and (iii) one or more RCA reagents.

7. The kit of claim 6, wherein the one or more RCA reagents are selected from one or more of a DNA polymerase, dNTPs, labelled probes and a reaction buffer.

8. The kit of claim 6, wherein the circular template comprises a sequence that is complementary to the RCA primer sequence and an AC rich nucleotide sequence.

9. The kit of claim 8, wherein the AC rich nucleotide sequence is at least 70% AC rich, at least 80% AC rich, or at least 85% AC rich.

10. The kit of claim 8, wherein the AC rich nucleotide sequence comprises the sequence as shown in SEQ ID NOs: 1-10.

11. The kit of claim 8, wherein the AC rich nucleotide sequence comprises one of the sequences as shown in SEQ ID NOs:36-40.

12. The kit of claim 7, wherein the DNA polymerase is phi29 DNA polymerase.

13. A method for detection of an analyte comprising:
   a) providinq the biosensor of claim 1;
   b) contacting a sample suspected of comprising the analyte with the biosensor under conditions for binding the analyte to the recognition moiety and desorption of the nucleic acid probe from the rGO, to provide rGO and an analyte-nucleic acid probe complex;
   c) separating the rGO from the analyte-nucleic acid probe complex;
   d) contacting the analyte-nucleic acid probe with a circular template comprising a sequence that is complementary to the RCA primer sequence under RCA conditions to amplify the circular template; and
   e) detecting a presence or an absence of the amplified circular template,
   wherein the presence of the amplified circular template indicates the presence of the analyte in the sample.

14. The method of claim 13, wherein the circular template comprises a sequence that is complementary to the RCA primer sequence and an AC rich nucleotide sequence.

15. The method of claim 14, wherein the AC rich nucleotide sequence is at least 70% AC rich, at least 80% AC rich, or at least 85% AC rich.

16. The method of claim 14, wherein the AC rich nucleotide sequence comprises one of the sequences as shown in SEQ ID NOs: 1-10.

17. The method of claim 14, wherein the RCA conditions comprise the presence of phi29 DNA polymerase.

18. The method of claim 14, wherein the analyte is a nucleic acid, protein or small molecule.

* * * * *